(12) United States Patent
Marchione et al.

(10) Patent No.: US 6,595,999 B2
(45) Date of Patent: Jul. 22, 2003

(54) DRILLING JIG FOR THE DETERMINATION OF THE AXIS OF A FEMUR HEAD PROSTHESIS

(75) Inventors: Andreas Marchione, Winterthur (CH); Thomas Willi, Breite Nürensdorf (CH); Heinrich Stutz, Frauenfeld (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 10/131,964

(22) Filed: Apr. 25, 2002

(65) Prior Publication Data

US 2002/0193801 A1 Dec. 19, 2002

(30) Foreign Application Priority Data

Apr. 27, 2001 (EP) .............................. 01810417

(51) Int. Cl.[7] .............................. A61B 17/17
(52) U.S. Cl. ................. 606/96; 606/102; 623/23.12
(58) Field of Search ................. 606/79, 80, 86, 606/87, 89, 96, 97, 98, 102, 130; 623/22.11, 22.12

(56) References Cited

U.S. PATENT DOCUMENTS 5,653,714 A * 8/1997 Dietz et al. ............... 606/87
5,817,098 A * 10/1998 Albrektsson et al. ......... 606/96
6,156,069 A   12/2000 Amstutz

FOREIGN PATENT DOCUMENTS

| DE | 11 64 019 B | 2/1964 |
| FR | 2 242 068 A | 3/1975 |
| FR | 2 478 462 A | 9/1981 |
| WO | WO 98 07393 A | 2/1998 |

OTHER PUBLICATIONS

Derek McMinn, "Birmingham Hip Resurfacing Operative Technique According to Derek McMinn" of Midland Medical Technologies (University of Birmingham Research Park, Birmingham, England); Booklet dated Birmingham Nuffield Hospital 1998., 24pgs.

* cited by examiner

Primary Examiner—David O. Reip
(74) Attorney, Agent, or Firm—Christie, Parker & Hale, LLP

(57) ABSTRACT

The invention relates to a drilling jig for the determination of the axis of a femur head prosthesis. A guide tube (6), around whose longitudinal axis (14) a sensing probe can be rotated, has a rounded head (7) which is supported in a housing (3) pivotable in all directions and fixable by first clamping elements (5), in order to fix its longitudinal axis in a desired angle. The housing (3) is displaceable in all directions transversely to its longitudinal axis with respect to a base part (1) which can be anchored to the femur head (10) and fixable by two clamping elements (4) in order to define the position of the longitudinal axis (14) of the guide tube (6) by rotation of a sensing probe around this longitudinal axis (14) relative to the cross-section of the femur neck (16).

10 Claims, 5 Drawing Sheets

Figure 4:
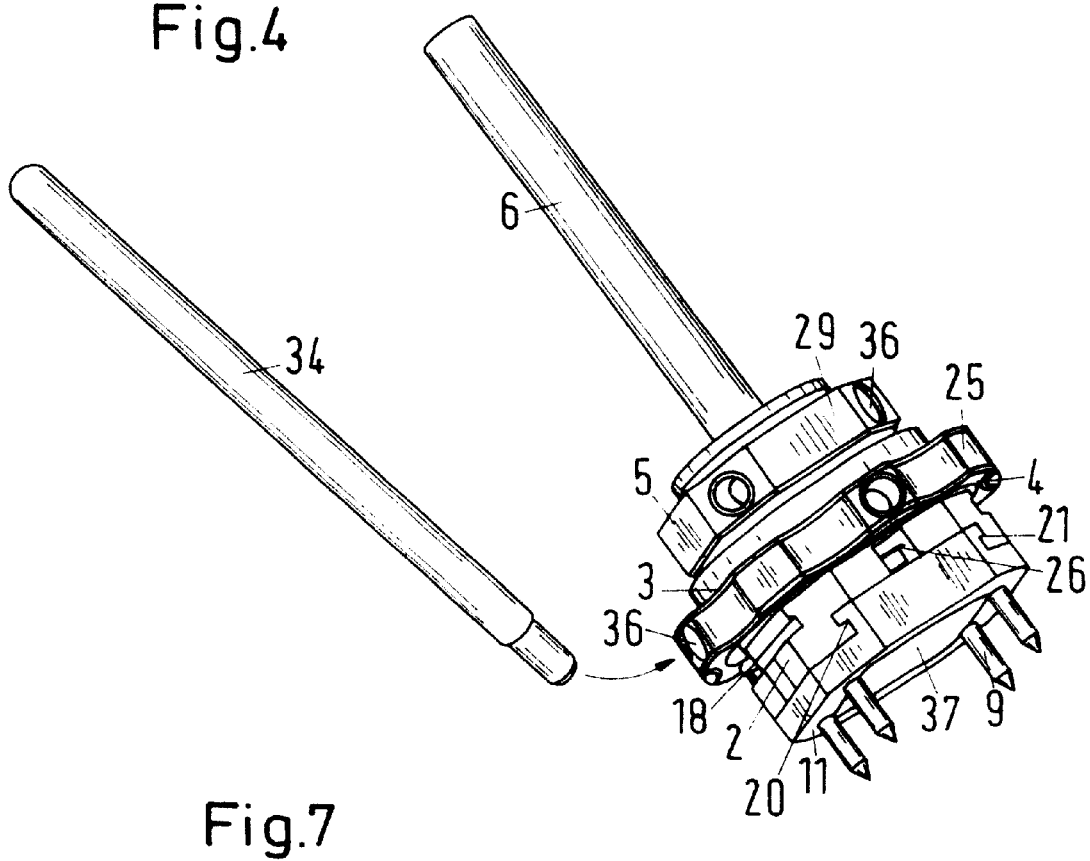

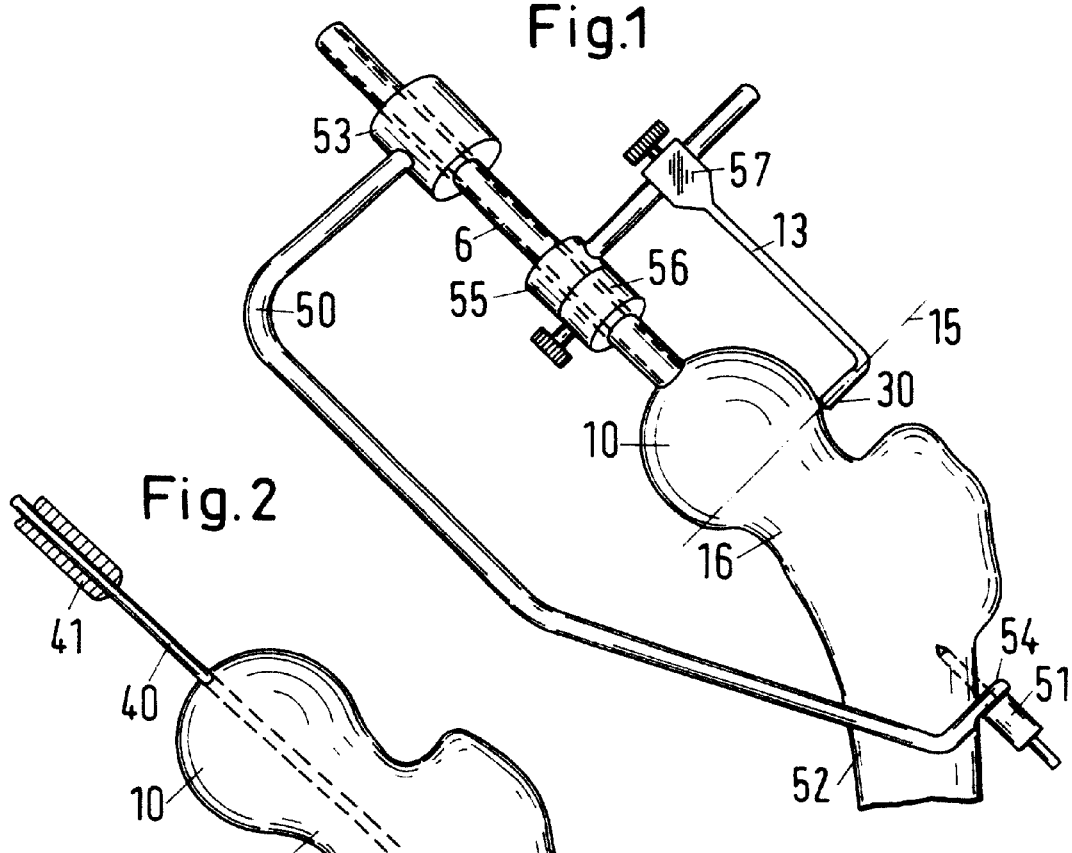
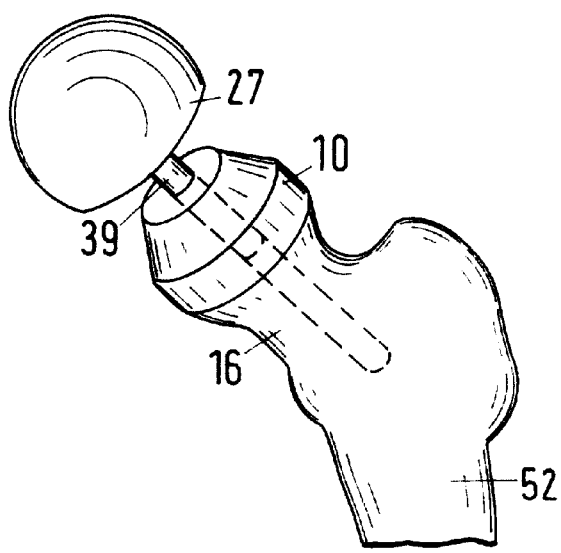

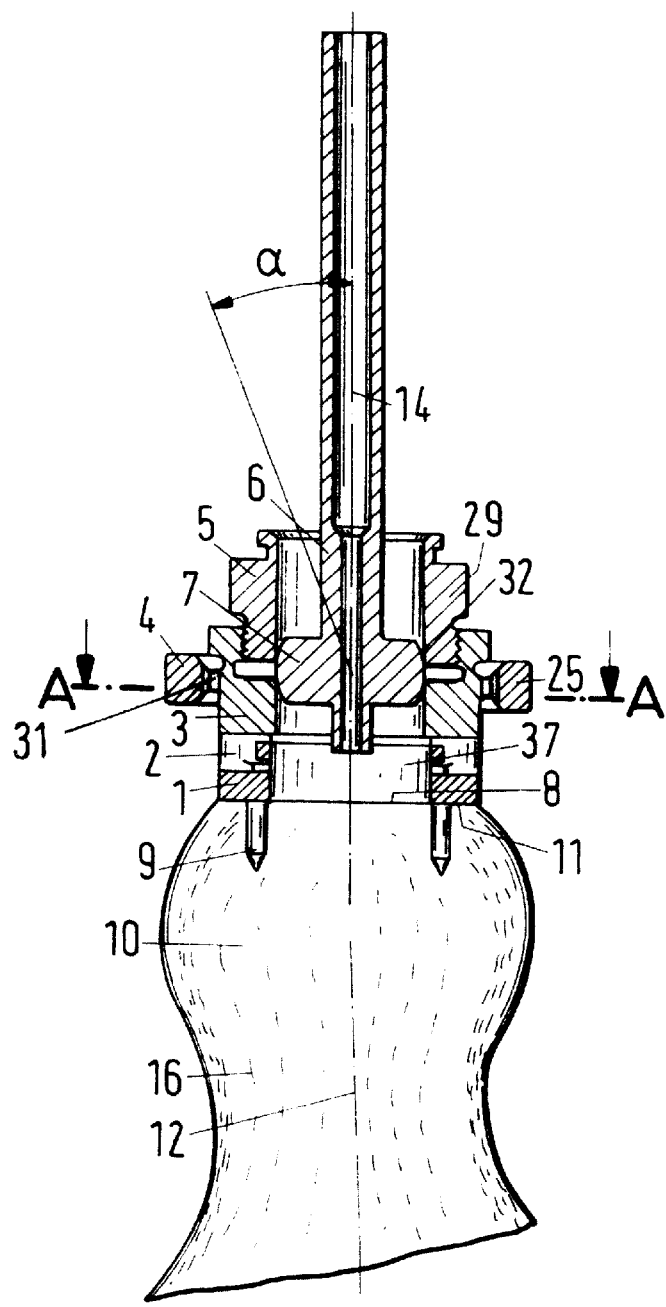
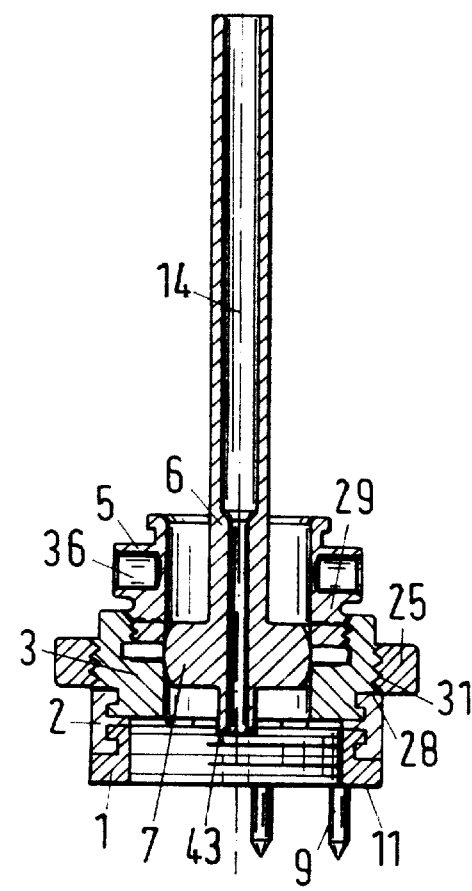
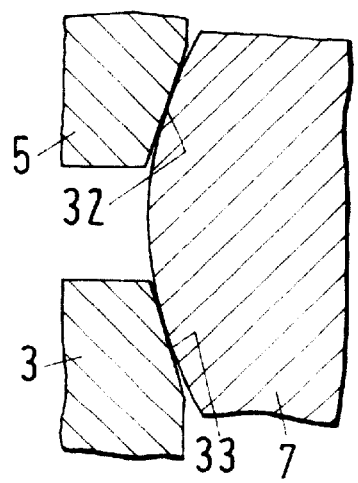

//DRILLING JIG FOR THE DETERMINATION OF THE AXIS OF A FEMUR HEAD PROSTHESIS

CROSS-REFERENCE TO RELATED APPLICATION

This application claims priority of European Patent Application No. 01810417.4, filed on Apr. 27, 2001.

The invention relates to a drilling jig for the determination of the axis of a femur head prosthesis having a guide tube around whose longitudinal axis a sensing probe can rotate in a plane of rotation to sense a neck of the femur at the transition to the femur head and to centre the position of the longitudinal axis with respect to the neck of the femur by a displacement of the guide tube.

Such drilling jigs are used to drive a Kirschner nail through the femur head deep into the neck of the femur and to use this Kirschner head as a centring and alignment device for the resurfacing tools with which the femur head is resurfaced to the internal dimensions of a matching femur head prosthesis. A corresponding operative technique is described in "Birmingham Hip Resurfacing Operative Technique According to Derek McMinn" of Midland Medical Technologies (University of Birmingham Research Park, Birmingham, England). The drilling jigs used there show a bearing yoke whose lower bearing is supported on a collar pin which first has to be driven in by the operator in the direction of the neck of the femur from the lateral side beneath the trochanter major. A circular guide, which is aligned to the lower bearing and which receives a guide tube longitudinally displaceable therein, is located in the upper part of the bearing yoke. A rotatable sensing probe is attached to the guide tube and the spacing to the lower edge of the head of the femur can be checked with its inwardly directed sensing tip. The contact point can be centred by a repeated raising of the guide tube from the head of the femur and by putting it down in a new position by means of the rotation of the sensing probe and subsequently lightly driven in a little in order to define the axis direction for a Kirschner nail or another drill. If a Kirschner nail was used, the guide tube is first pulled off upwardly and the bearing yoke is subsequently withdrawn. The guide tube and the sensing probe can again be set onto the Kirschner nail for the visual control of the centring. This method has the disadvantage that, for the setting of the collar pin at a spacing beneath the trochanter major, a relatively large region must additionally be opened which is outside the actual operation region in which the head of the femur is resurfaced and a femur head prosthesis put on. A further difficulty lies in the fact that the effective neck angle of the neck of the femur should be taken into account in the selection of the driving in point for the collar pin.

The invention is intended to improve these circumstances. It has the object of providing an expedient drilling jig. This object is satisfied in accordance with the independent claim 1 in that the guide tube is pivotally mounted with a rounded head in a housing and can be fixed with first clamping elements at a designated pivot angle α of its longitudinal axis relative to the longitudinal axis of the housing, and in that the housing can be displaced in any direction transversely to its longitudinal axis with respect to a base part with a recess which is provided for the fastening to a femur head and can be fixed in a designated displacement position by second clamping elements.

The invention has the advantage that the angular position of the longitudinal axis of the guide tube relative to the support surface of the base part and the point of intersection of the longitudinal axis with the plane of the support surface can be freely chosen. It is sufficient if the operator makes a first resection area at the femur head as a base for the base part, with this area only having to be approximately perpendicular to the axis of the neck of the femur. As soon as the base part is fastened to the first resection area, for which it has, for example, anchoring pins at its lower side for driving in, the parallelism of the guide tube to the axis of the neck of the femur can first be checked and set from two different directions and subsequently the longitudinal axis of the guide tube can be displaced in the plane of the support surface until an optimum distribution of the cross-section of the neck of the femur is achieved during the rotation of the sensing probe.

Advantageous further developments of the invention result from the dependent claims 2 to 10.

The division into two independent clamping elements allows the pivot angle α and the position of the longitudinal axis of the guide tube to be set in succession and independently of one another. Undercut guides of the base part and the housing engage into a displacement part located between them. Since the guides intersect when viewed in the direction of the longitudinal axis of the housing, the housing moves like a cross slide relative to the base part. The base part and the displacement part have a recess when viewed in the direction of the longitudinal axis of the housing, inside which the lower end of the guide tube can be displaced. When a clamping nut is adjustable on an external thread of the housing in the direction of the longitudinal axis of the housing and radially projects further from the longitudinal axis, torques are produced on the guides of the displacement part which result in an elastic deformation of the displacement part when this is deliberately weakened by flexion spring sections. This effect is amplified more when the upwardly directed guide surface of the guides of the housing has a slightly convex curvature. The guides of the housing and the base part can be simultaneously blocked in this way with a clamping nut.

The head of the guide tube is spherically rounded and sits on a bearing surface of the housing. The oblique shoulder of a clamping sleeve in the housing which is adjustable in its thread presses the head into its bearing surface and thus blocks it in a designated angular position.

It has quite generally been found in the positioning of a guide tube with a sensing probe which can rotate on it, that a sensing and centring of the neck of the femur directly beneath the femur head result in a good distribution of the harder cortex layer onto the femur head prosthesis if the sensing radius $r_i$ from the axis of rotation to the tip of the sensing probe is smaller than the inner radius $R_i$ of the femur head prosthesis at its lower edge by an amount of 1.2 to 2.5 millimeters. This makes necessary a whole kit of femur head prostheses with associated sensing probes. With a sufficiently fine gradation, the sensing radius can be chosen smaller than the inner radius of the femur head prosthesis at its lower edge by an amount of between 1.5 to 1.9 millimeters. The ideal inner radius of the femur head prosthesis at its lower edge for the associated sensing probe, which can just rotate in the centred state, would then be 1.5 to 1.9 millimeters larger than the radial spacing of the sensing tip.

Figure 7:
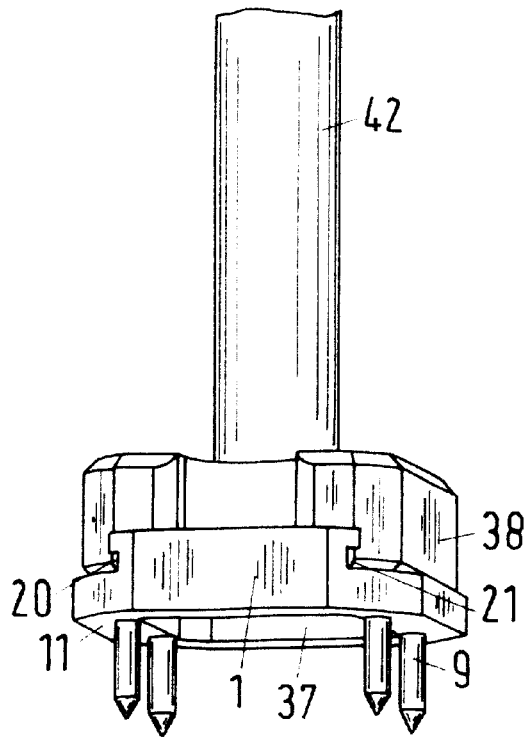
Figure 8:
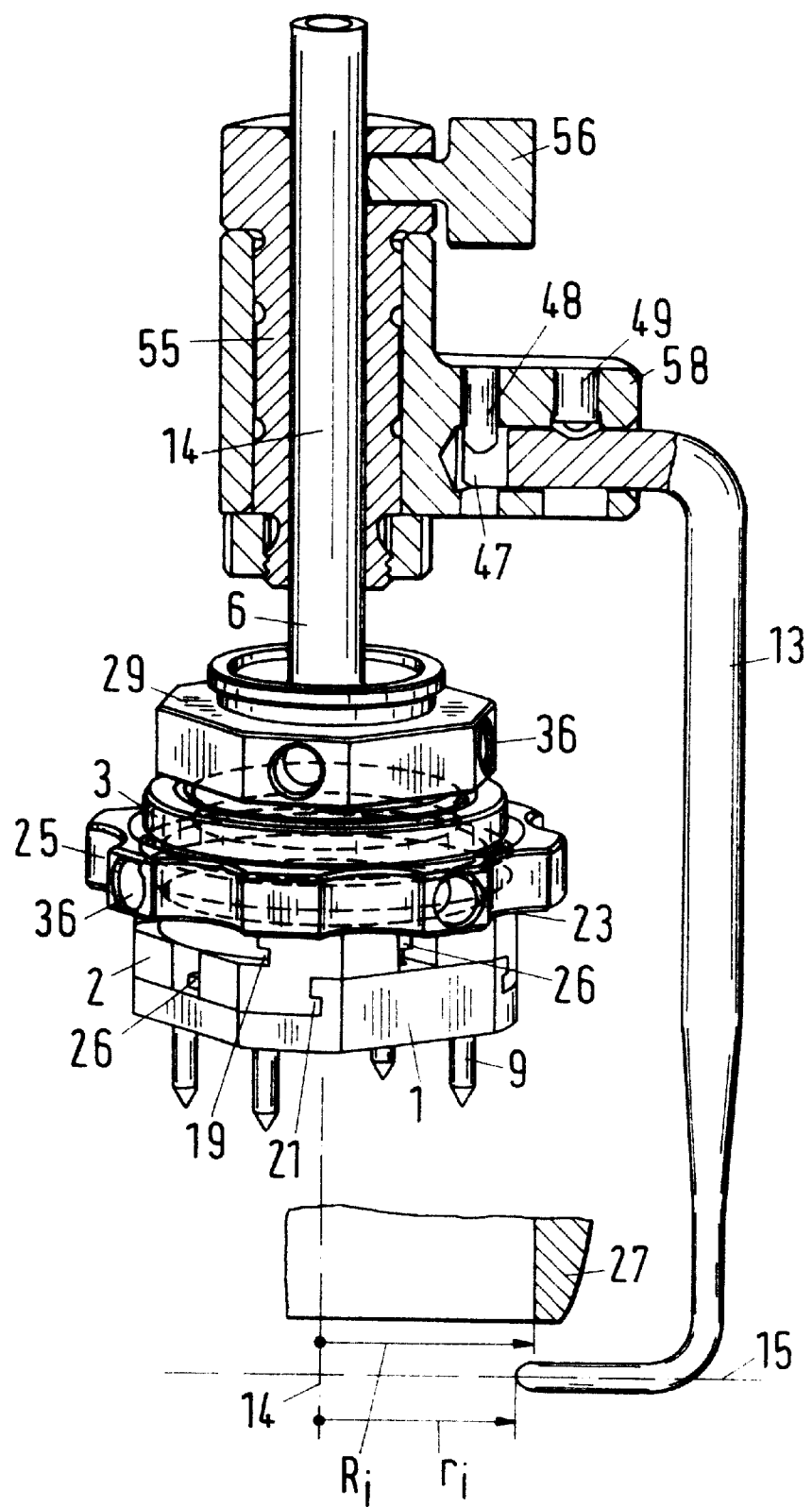
Figure 9:
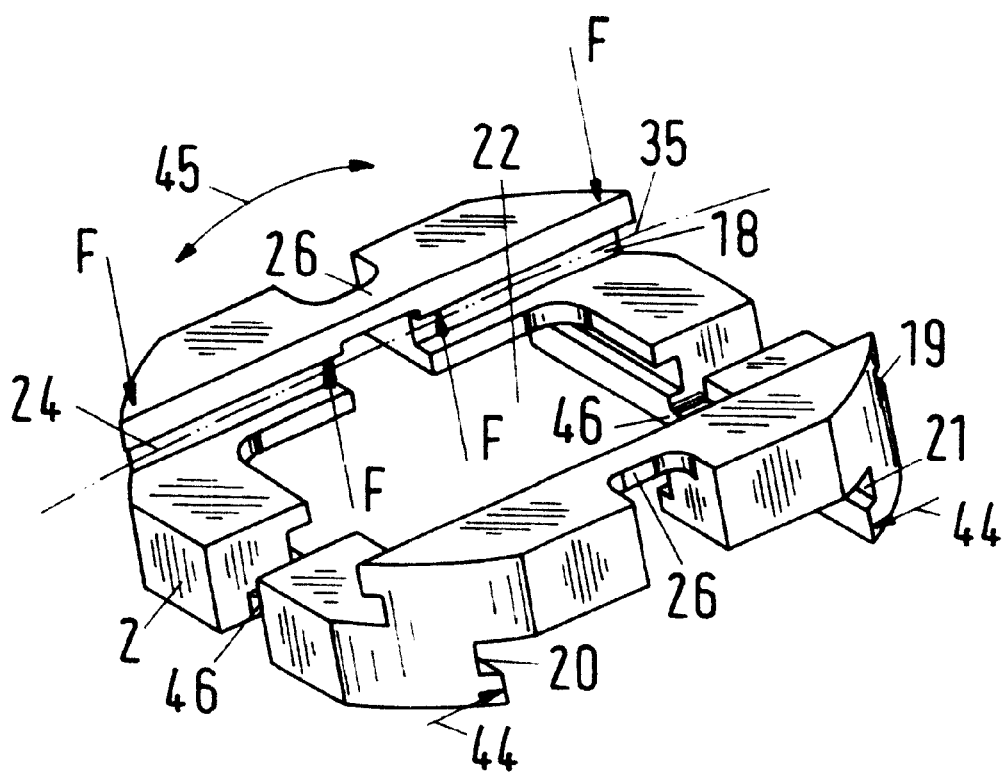

The invention is described in the following by way of embodiments. There are shown:

FIG. 1 schematically from the known prior art, a drilling jig according to Derek McMinn and Midland Medical Technologies;

FIG. 2 schematically from the prior art, a hollow drill centred on a Kirschner nail;

FIG. 3 schematically from the prior art, a femur head prosthesis provided with a stem prior to being driven in to a pre-surfaced femur head;

FIG. 4 schematically, a general view of a drilling jig of the invention;

FIG. 5 schematically, a first longitudinal section through the drilling jig of FIG. 4 in the driven-in state at a femur head;

FIG. 6 schematically, a second longitudinal section through the drilling jig of FIG. 4 offset by approximately 45°;

FIG. 7 schematically, a view of the base part of the drilling jig of FIG. 4 with an associated instrument for driving it in and out;

FIG. 8 schematically, a side view of a drilling jig in accordance with the invention having a rotatable sensing arm;

FIG. 9 schematically, a general view of a coupling part for a drilling jig in accordance with FIG. 4; and FIG. 10 schematically, greatly magnified, the clamping of the head of the guide tube in FIG. 6.

The same reference symbols have been used for the same functions in the figures.

The figures show a drilling jig for the determination of the axis of a femur head prosthesis. A guide tube 6, around whose longitudinal axis 14 a sensing probe can rotate, has a rounded head 7 which can be pivoted to all sides and is supported in a housing 3 in a manner fixable with first clamping elements 5 in order to fix its longitudinal axis at a desired angle. The housing 3 can be displaced to all sides transversely to its longitudinal axis with respect to a base part 1 which can be anchored to the femur head 10 and can be fixed with second clamping elements 4 in order to define the position of the longitudinal axis 14 of the guide tube 6 relative to the cross-section of the femur neck 16 by the rotation of a sensing probe around this longitudinal axis 14.

The conventional operative technique will be described briefly with reference to FIGS. 1, 2 and 3. After the site of the operation has been opened to below the trochanter major at the femur 52, a collar pin 51 is driven in laterally in the direction of the femur neck axis 12. A bearing yoke 50 has a lower bearing 54 and a circular guide 53 for an axially movable guide tube 6. A vertical adjustment facility 56 is attached to the guide tube 6 in the form of an adjustable abutment for a bearing 55 which is rigidly connected to a sensing probe 13 via a lateral adjustment facility. The lower bearing 54 of the bearing yoke 50 is suspended at the collar pin 51 and the guide tube 6 is set in the presumed centre of the femur head 10 at the upper side. An inwardly directed sensing tip 30 of the sensing probe is brought by the vertical adjustment facility 56 into a plane of rotation 15 located at the transition to the femur neck 16. The radial spacing of the sensing tip 30 is selected by means of the lateral adjustment facility 57 to be so large that a rotation of the sensing tip 30 around the femur head is possible. The guide tube is displaced into a new fitting point for so long until the spacings of the opposite points to the sensing tip are approximately equal. The centred guide tube is anchored in the femur head 10 by a blow and determines the direction to the lower bearing 54. The guide tube fixed in this manner serves as a guide or drilling jig for a Kirschner nail or a drill tool which are driven through the femur neck 16 in accordance with FIG. 2. The guide tube 6, bearing yoke 50 and sensing probe 13 can subsequently be withdrawn. The freely projecting Kirschner nail now serves for the centration and guiding of a cannulated drill 41 and further processing tools until a worked femur head 10 in accordance with FIG. 3 has been created into which a femur head prosthesis 27 can be driven which, in this case, is pre-centred with a stem 39 before its inner surfaces sit on the femur head 10.

FIGS. 4, 5, 6 and 10 show an apparatus of the invention which replaces an arrangement in accordance with FIG. 1. A base part 1, in the form of a frame with a cut-out 37, has a support surface 11 and projecting anchoring pins 9 at its lower side. The base part is held by two undercut guides 20, 21 in a displacement element 2 which can be displaced along the guides 20, 21. Two undercut guides 18, 19 likewise engage into the displacement element 2 from above from a housing 3, but are arranged transversely to the guides 20, 21 of the base part 1. The housing 3 is thus displaceable transversely to its longitudinal axis 17 to a limited extent like a compound table 23.

The lower edge 28 of a second clamping element 4 in the form of a clamping nut 25, which can be moved up and down on an outer thread 31 of the housing 3, presses onto the projecting corner regions of the displacement element 2, that is approximately at the point where—seen from above—the guides 18, 19 and 20, 21 intersect. The displacement element 2 would be blocked at the guides 18, 19 simply by the seating of the clamping nut which presses the displacement element downwardly into the lower guide surface 35 within the range of the clearance. However, the guides 20, 21 of the base part should also be blocked before the guides 18, 19 of the housing 3 are definitively blocked. For this reason, the lower guide surface 35 has a slightly convex curvature and the guide rails of the displacement element are each tapered at the centre to form a flexion spring 26 to stress the displacement element 2 in its elastic region as the corner regions of the displacement element are pressed down and as a matching to the curvature of the guide surfaces 35 takes place such that all guides 18, 19, 20, 21 are blocked. The housing 3 can thus be blocked in any position by the clamping nut 25. A rod-shaped arm 34 can be inserted into radial bores 36 (at their periphery) for the enlargement of the torque at the clamping nut 25. The same tool can also be inserted for radial bores 36 at the first clamping element 5 which is designed as a clamping sleeve 5.

A displacement element 2 is shown in FIG. 9 which is also designed as a closed frame with a recess 22. The guide regions are each divided into two halves which are connected by a flexion spring 26 at their centre. It is actually sufficient to provide a convex guide surface 35 and flexion springs 26 only in one plane of the guides, for example for the upper guides 18, 19, in order to achieve a clamp movement 44 at the lower guides 20, 21. Since the guides 20, 21 of the displacement part 2 are supported from the outside by the displacement part and the displacement part 2 performs a clamping movement 44 due to the matching to the curvature 24 of the guide surfaces 35 in the upper guides 18, 19 transversely thereto in the lower plane of the lower guides 20, 21, the lower guides 20, 21 are also blocked. Forces F are drawn in at the rear guide 18 which, with a curved guide surface 35 of the housing 3, indicate an elastic deformation 45 and, as a consequence thereof, the clamping movement 44 which is not shown here. The displacement element is provided in the example shown with two further flexion springs 46 which allow flexion at the lower guides 20 and 21. This is only a necessity because the dimensions of the guides 18, 19, 20, 21 are identical and because flexion springs are necessary when the displacement part 2 is installed in reverse.

FIGS. 5, 6 and 10 furthermore show the adjustment possibilities of the guide tube 6. The operator will never be able to apply a first resection area 8 at the femur head exactly perpendicular to the neck axis 5. He must take up the base part 1 in accordance with FIG. 7 using a pick-up tool 38 which engages into the guides 20, 21 and first drive the base part 1 as centrally as possible on this first resection area 8 by hitting the tool shaft 42 with a hammer. The tool is subsequently withdrawn along the guides 20, 21 and the adjustment element 2 already connected to the housing 3 is pushed on. For this purpose, the clamping nut 25, on the one hand, is loosened so far that pushing on along the guides 20, 21 is possible and the clamping sleeve 29, on the other hand, is loosed so far that the opening 43 of the guide tube 6 can be raised over and beyond the edge of the base part 1. When the head 7 of the guide tube sits on its bearing surface 33 at the housing 3, the opening 43 projects so far into the cut-out 37 that the base part 1 and the housing 3 are not unintentionally released from one another by a lateral displacement. A further advantage lies in the fact that the opening extends up to close to the resection area 8 and accordingly later supports a drill tool well. The cut-out 37 provides sufficient space for chip reception for a drill tool which produces chips.

The actual alignment of the longitudinal axis 14 of the guide tube 6 takes place in a first step in that the guide tube is sighted from the side from two directions offset by around 90° and is brought into a position parallel to the femur neck axis 12 in order to be subsequently fixed with its clamping sleeve 29 on its bearing surface 33 at the pivot angle α found in this manner. The arm 34 (FIG. 4) can provide the torque required for this and press the oblique shoulder 32 of the clamping sleeve 29 onto the head. After the parallel position of the longitudinal axis 14 of the guide tube 6 has been ensured, its displacement into the centre of the femur neck 16 takes place. Up to 15°, for example, can be provided as the pivot angle α out of the centre position.

In FIG. 8, a sensing probe 13 is held with its end in a receiving bore of a rotatable arm 58 by a snap mechanism 49 and positioned by a pin 48 at its end designed as a fork 47. This allows a simple replacement of sensing probes 13 with sensing tips 30 having differently large spacings to the longitudinal axis 14 of the guide tube 6. The arm 58 is arranged at a separate bearing 55 which extends concentrically to the guide tube 6, with the vertical adjustment facility 56 of the bearing 55, and thus that of the sensing tip 30, taking place with a setting screw. After the appropriate sensing height has been set at the femur neck, the sensing probe is rotated and the housing movable like a cross slide is displaced with the guide tube until the desired distribution of the cross-section of the femur neck 16 is achieved. The clamping nut 25 is subsequently tightened in order to fix the desired position in the guides 18, 19, 20, 21. The sensing probe 13 can be withdrawn to the side, the bearing 55 with the arm 58 can be withdrawn upwardly after the loosening of the setting screw for the vertical adjustment facility 56. The four anchoring pins 9 shown at the base part 1 provide sufficient stability to guide a drill tool in the direction of the longitudinal axis 14 using the guide tube 6.

It has been found when determining the position by rotation using sensing with sensing probes 13, whose tip 30 corresponds to a sensing radius of $r_i$, and which can just be rotated around the femur neck 16 below the femur head 10, this sensing radius $r_i$ can in each case be associated with a matching femur head prosthesis 27 with an inner radius $R_i$ at the lower edge which is greater by a constant amount. For example, the value pairs

| $r_i$ (mm) | 14 | 15 | 22 |
|---|---|---|---|
| $R_i$ (mm) | 15.7 | 16.7 | 23.7 | result with a constant amount of 1.7 millimeters.

What is claimed is:

1. A drilling jig for the determination of the axis of a femur head prosthesis (27) having a guide tube (6) around whose longitudinal axis (14) a sensing probe (13) can rotate in a plane of rotation (15) to sense a neck (16) of the femur at the transition to its femur head (10) and to centre the position of the longitudinal axis (14) with respect to the neck (16) of the femur by a displacement of the guide tube (6), wherein the guide tube (6) is pivotally mounted with a rounded head (7) in a housing (3) and can be fixed with first clamping elements (5) at a designated pivot angle α of its longitudinal axis (14) relative to the longitudinal axis (17) of the housing (3); and the housing can be displaced in any direction transversely to its longitudinal axis (17) with respect to a base part (1) with a cut-out (37) which is provided for the fastening to a femur head (10) and can be fixed in a designated displacement position by second clamping elements.

2. A drilling jig in accordance with claim 1, wherein the first clamping elements (5) for the fix of the pivot angle a and the second clamping elements (6) for the fix of the displacement position can be actuated independently of one another.

3. A drilling jig in accordance with claim 1, wherein the housing (3) and the base part (1) have undercut guides (18, 19; 20, 21) which engage into a displacement part (2) lying therebetween in order to form a cross slide (23).

4. A drilling jig in accordance with claim 3, wherein the second clamping elements (4) are formed by a clamping nut (25) at the outer periphery of the housing (3), with the clamping nut (25) pressing onto the displacement part (2) and the latter being designed elastically such that its elastic deformation blocks the slide movements in the guides (18, 19; 20, 21).

5. A drilling jig in accordance with claim 4, wherein at least one guide surface (35) of the guides (18, 19) is convexly curved at the housing (3) contrary to the clamping nut (25); and in that the displacement part (2) is formed as a flexion spring (26) in the region of this curvature (24) in order to prevent a displacement along the guides (18, 19) of the housing (3) as the curvature adapts under the effect of the clamping nut (25).

6. A drilling jig in accordance with claim 5, wherein the clearance in the guides (20, 21) of the base part (1) is so tightly dimensioned that the guides (20, 21) of the base part (1) are blocked before the adaptation to the curvature of the guides (18, 19) of the housing (3) has been fully completed.

7. A drilling jig in accordance with claim 1, wherein the first clamping element (5) is a clamping sleeve (29) with an outer thread (31) which can be adjusted in the direction of the housing's longitudinal axis (17) and which has an oblique shoulder (32) at its inner side which presses the rounded head (7) of the guide tube (6) onto a bearing surface (33) of the housing (3).

8. A drilling jig in accordance with claim 7, wherein the clamping sleeve (29) and the clamping nut (25) have radial bores (36) distributed over the periphery into which a rod-shaped arm (34) can be inserted to produce a sufficient clamping torque.

9. A drilling jig in accordance with claim 8, wherein a plurality of exchangeable sensing probes (13) are present which form a kit with matching ball-shaped femur head prostheses (27) which have an inner radius $R_i$ at the lower edge, with the sensing tip (30) of an associated sensing probe (13) being rotatable at a radius $R_i$ around the longitudinal axis (14) of the guide tube (6), which is smaller than the inner radius $R_i$ by an amount between 1.2 to 2.5 millimeters.

10. A drilling jig in accordance with claim 9, wherein the sensing radius is smaller than the inner radius $R_i$ of an associated femur head prosthesis by an amount between 1.5 and 1.9 millimeters.

* * * * *